(12) United States Patent
Nickson

(10) Patent No.: US 7,161,364 B1
(45) Date of Patent: Jan. 9, 2007

(54) DERMAL PHASE METER WITH REPLACEABLE PROBE TIPS

(75) Inventor: Steven W Nickson, Derry, NH (US)

(73) Assignee: Nova Technology Corporation, Portsmouth, NH (US)

( * ) Notice: Subject to any disclaimer, the term of this patent is extended or adjusted under 35 U.S.C. 154(b) by 0 days.

(21) Appl. No.: 10/908,327

(22) Filed: May 6, 2005

Related U.S. Application Data

(60) Provisional application No. 60/521,520, filed on May 11, 2004.

(51) Int. Cl.
*G01R 31/02* (2006.01)
*G01R 31/28* (2006.01)

(52) U.S. Cl. .................................. 324/754; 324/158.1
(58) Field of Classification Search ............... 600/547, 600/546, 170, 171, 175; 324/133
See application file for complete search history.

(56) References Cited

U.S. PATENT DOCUMENTS

| | | | |
|---|---|---|---|
| 3,929,018 A * | 12/1975 | Turner | 374/158 |
| 5,297,055 A | 3/1994 | Johnstone | |
| 5,413,107 A | 5/1995 | Oakley et al. | |
| 5,479,930 A | 1/1996 | Gruner et al. | |
| 5,961,471 A * | 10/1999 | Nickson | 600/546 |
| 6,106,517 A | 8/2000 | Zupkas | |
| 6,186,959 B1 * | 2/2001 | Canfield et al. | 600/559 |
| 6,370,426 B1 | 4/2002 | Campbell et al. | |
| 6,461,037 B1 * | 10/2002 | O'Leary | 374/158 |
| 6,603,297 B1 * | 8/2003 | Gessford et al. | 324/72.5 |
| 6,688,906 B1 * | 2/2004 | Kimbley | 439/482 |
| 2002/0107502 A1 | 8/2002 | Hung et al. | |
| 2003/0171700 A1 | 9/2003 | Martin et al. | |

\* cited by examiner

*Primary Examiner*—Paresh Patel
*Assistant Examiner*—Roberto Velez
(74) *Attorney, Agent, or Firm*—George A. Herbster

(57) ABSTRACT

A probe for a dermal phase meter includes a handle with a removable extension that terminates with a displaceable center conductor. A replaceable tip attaches to the distal end of the extension and includes a center conductor that engages the center conductor in the extension and an outer conductor that establishes electrical connection through the extension. Substituting different replacement tips provides a probe with an articulation capability.

11 Claims, 6 Drawing Sheets

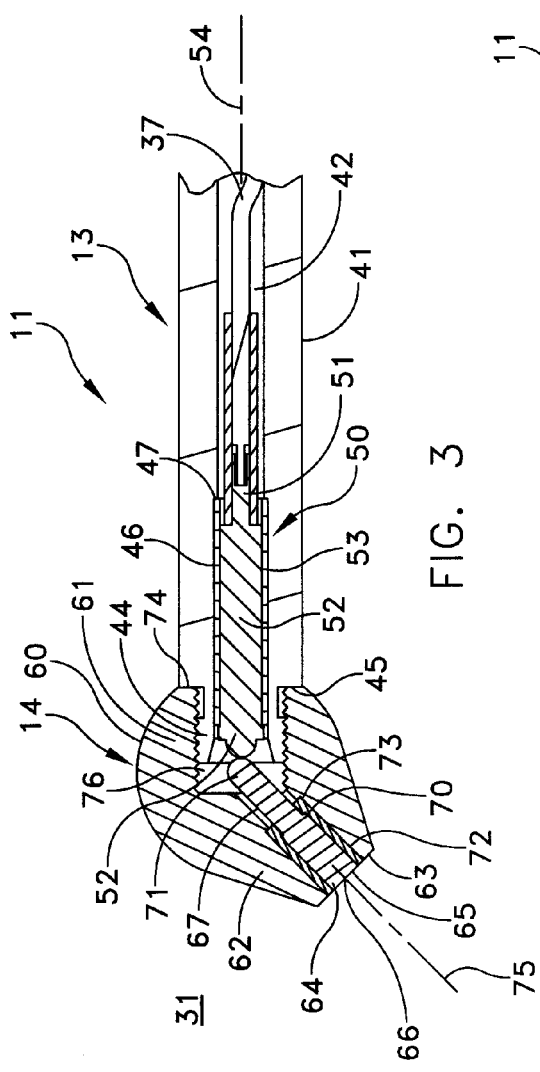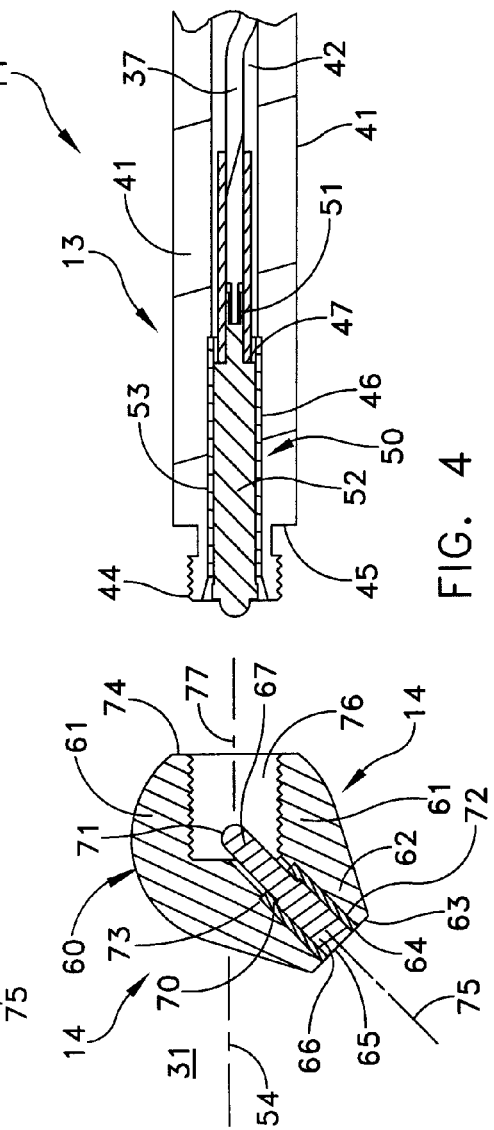

DERMAL PHASE METER WITH REPLACEABLE PROBE TIPS

FIELD OF THE INVENTION

This invention generally relates to dermal phase meters and more specifically to a probe that can broaden the applications for such dermal phase meters.

DESCRIPTION OF RELATED ART

Over the years there has been a growing interest in measuring the relative hydration of a substrate, such as the skin, for determining certain biophysical characteristics. U.S. Pat. Nos. 5,961,471 and 6,370,426 disclose different probes for obtaining such measurements. U.S. Pat. No. 5,961,471 to Nickson particularly discloses a probe for biophysical skin measurements that includes a disposable sensor and a handle for receiving a cable from a measurement device. A socket on the handle electrically interconnects with the cable. This disposable sensor removably engages the socket. When engaged, the sensor electrically interconnects with the cable for providing measurement signals concerning the biophysical skin measurement.

It now appears that measurements from such dermal phase meters may be used in models to indicate other medical conditions by applying a sensor to internal tissue, such as in the oral and anal cavities. Certain investigations are determining the efficacy of modeling the evaluation of oral mucositis by making measurements at multiple regions in the oral cavity for erythema and ulcerations. Other investigations are directed to determining the efficacy of such instruments in evaluating trauma, particularly hemorrhagic shock.

Probes, such as shown in the above-identified references, tend to be cumbersome and have a sensing surface that lies in a measurement plane that is orthogonal to a probe axis. To extend dermal phase meters to these new modalities, it has become important that the probes must be smaller. However, even smaller probes may be difficult to position within a cavity when the measurement plane is orthogonal to the probe axis. However, a probe with a fully articulated measurement plane is complex and not particularly adapted to miniaturization. What is needed is a probe that provides an articulation function, that is simple to use and that is economical to produce.

SUMMARY

Therefore it is an object of this invention to provide a probe that is adapted for allowing the aspect of the measurement plane to be altered with respect to a probe axis.

Another object of this invention is to provide a probe that is adapted for altering the aspect of the measurement plane to the probe axis that can also reduce manufacturing costs without degrading electrical integrity.

Yet another object of this invention is to provide a probe that is adapted for altering the aspect of a measurement plane to a probe axis that is easy to use.

In accordance with one aspect of this invention a dermal phase meter system includes a data processing system and a probe for providing input to the data processing system. The probe comprises a set of replaceable probe tips, each being capable of obtaining a measurement in measurement plane. A probe tip support lies along a probe axis and includes a connector at a proximal end thereof for establishing a connection to the data processing system. An electromechanical connector on the distal end of said probe tip support and on each probe tip enables the attachment and detachment of a probe tip to the distal end of the probe tip support. Different probe tips provide different aspects between the probe axis and the measurement plane.

In accordance with another aspect of this invention a probe for a dermal phase meter includes a handle, an extension and a replaceable probe tip. The handle has an externally insulated conductive body and a proximal electrical connector supported thereby. The extension comprises an externally insulated conductive element with a central passage along a probe axis attached to a distal end of the handle body. The extension has a threaded connection thereon and an axially displaceable spring biased electrode assembly in the passage. The replaceable probe tip has an externally insulated conductive body and first and second passages lying on first and second intersecting axes. An insulator is in the first passage. A conductor supported by the insulator extends into the second passage. An internally threaded portion on the probe tip extends along the second axis for attachment to and detachment from threaded connection on the extension with the probe and second axes being coincident.

BRIEF DESCRIPTION OF THE DRAWINGS

The various objects, advantages and novel features of this invention will be more fully apparent from a reading of the following detailed description in conjunction with the accompanying drawings in which like reference numerals refer to like parts, and in which:

FIG. 3 is an enlarged detail of the distal end of the probe shown in FIG. 2;

FIG. 4 is an enlarged view corresponding to FIG. 3 with a probe tip separated from a probe handle;

DESCRIPTION OF ILLUSTRATIVE EMBODIMENTS

Figure 1:
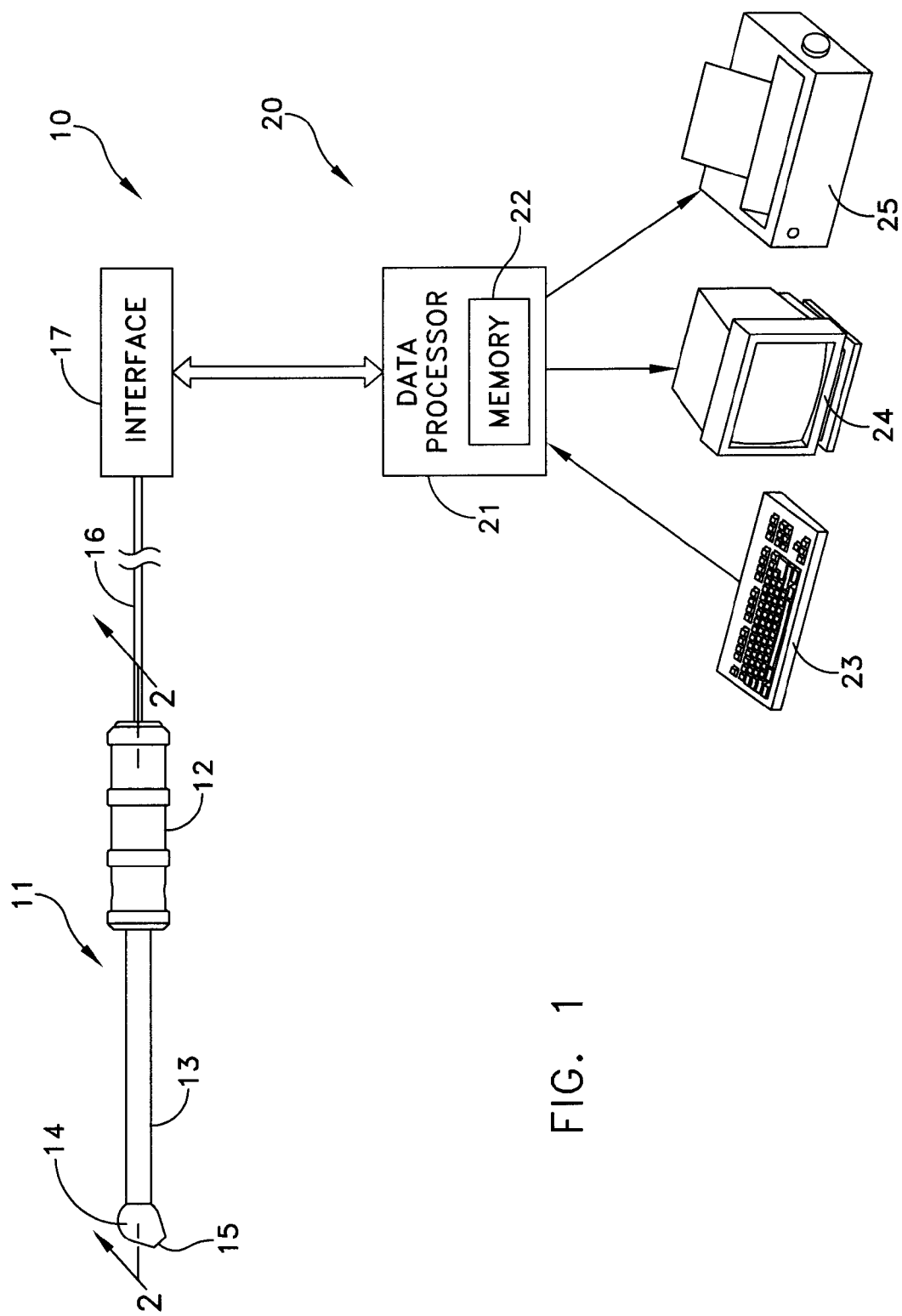
FIG. 1 schematically depicts a dermal phase meter with a probe having a given aspect between a probe axis and a measurement plane.

FIG. 1 depicts one embodiment of a dermal phase meter 10 that includes a probe 11. The probe 11 includes a probe tip support in the form of a handle 12 at a proximal end and an extension 13 intermediate the handle 12 and a distal probe tip 14. The distal tip 14 has measuring surface 15 that can have a variety of forms. Essentially the measuring surface 15 lies in a measurement plane defined by two electrodes spaced by an insulating medium.

Other conductors 16 couple the electrodes in the distal tip 14 to an interface 17 that includes various electronics for sampling data to read the signal developed across the electrodes at some sampling frequency. A data processing system 20 controls the operation of the probe 11 through the interface 17. The data processing system 20 includes a data processor 21 with a memory 22, an input device shown in the form of a keyboard 23, and one or more output devices, shown as a video display 24 and a hard copy printing device 25. As will be apparent the specific implementation of the data processing system 20 can take many forms that are well within the purview of persons of ordinary skill in the art.

Figure 2:
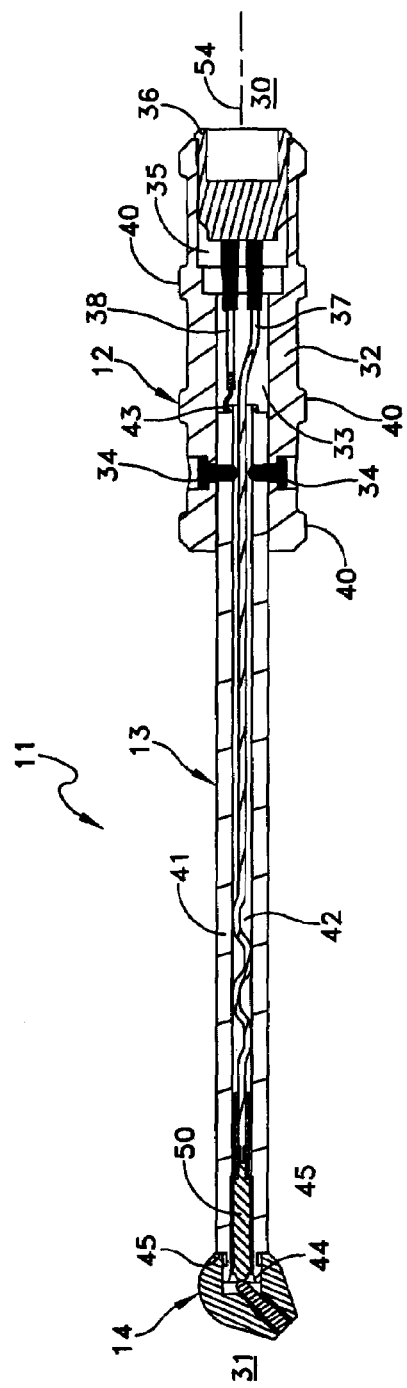
FIG. 2 is a longitudinal cross section of the probe shown in FIG. 1.
Figure 6:
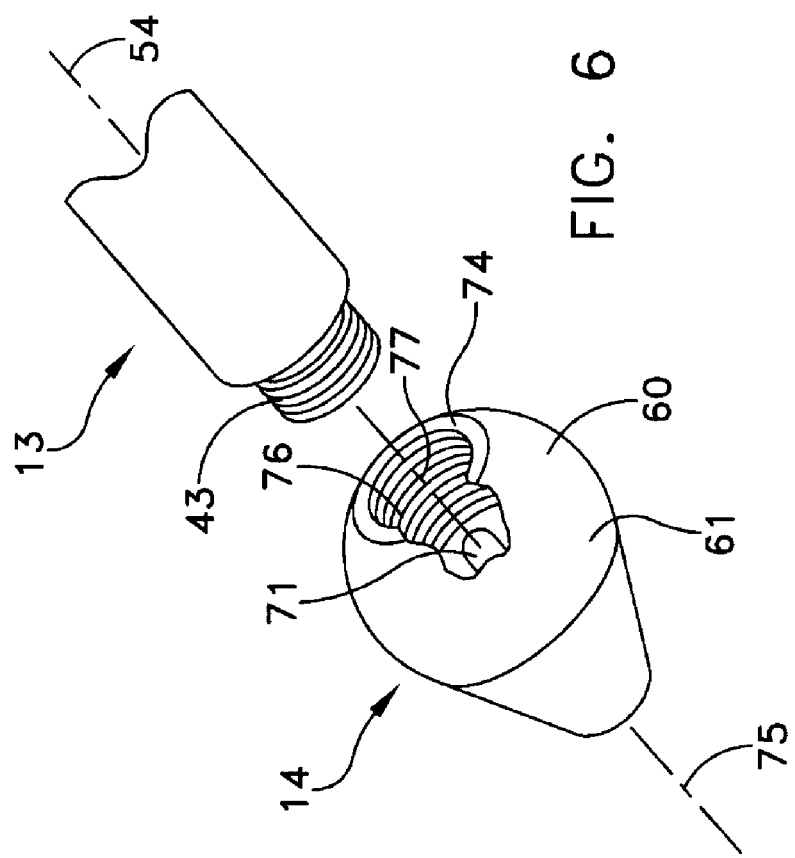
FIG. 6 is a perspective view of a probe tip taken from the proximal end.

Referring now to FIG. 2, the probe 11 extends from a proximal end 30 at the handle 12 to a distal end 31 at the probe tip 14. The handle 12 has a generally cylindrical body 32 with a receptacle 33 to receive the extension 13. In this specific embodiment, a fastener attaches the cylindrical body 32 to the extension 13. As an example, in FIG. 2 diametrically opposed machine screws 34 extend radially through the cylindrical body 32 to engage the extension 13.

The proximal end of the handle 12 also has a proximally facing receptacle 35 that receives a proximal electrical connector 36. The connector 36 is adapted to receive a cable, such as the cable 16 shown in FIG. 1. The connector 36 also has two conductors 37 and 38. The conductor 37 is insulated and extends from the connector 36 through the extension 13 to the tip 14 as described below. The conductor 38 attaches to the extension 13 by soldering or other means.

The cylindrical body 32 is formed from an engineering polymer, such as Delrin®, with axially spaced, circumferential beads or bands 40. The beads or bands 40 form a gripping surface for the probe 11. The cylindrical body 32 thereby constitutes an insulated handle.

In this embodiment, the extension 13 is formed as a tube 41 with a central passage 42. Although not shown, the exterior surface of the tube 41 has an insulating coating so it acts as an externally insulated conductive extension. This allows the tube 41 to act as a conductor for the signals received from the tip 14 and be handled without electrical contact by personnel. A proximal radial surface 43 provides a connection point for the conductor 38.

Referring now to FIGS. 2 through 4, at the distal end 31, the tube 41 terminates in an externally threaded head portion 44 and radial shoulder 45. As shown more clearly in FIGS. 3 and 4, an enlarged, elongated chamber 46 in the tube 41 extends to an internal radial shoulder 47. This chamber 46 receives an axially displaceable spring biased conductor assembly 50, also shown in FIG. 2. Referring again to FIGS. 3 and 4, such assemblies are commercially available and comprise a proximal end connection 51 for the conductor 37, a center conductor 52 and an insulating housing 53. The assembly 50 includes an internal spring, not shown, that biases the center conductor 52 distally, along a probe axis 54. This structure provides a continuous conductive path between the center conductor 52 and the end connection 51 even as the center conductor 52 moves axially within the insulating housing 53. A P3325 Series Probe manufactured by Everett Charles Technologies is an example of such an assembly 50.

Figure 5:
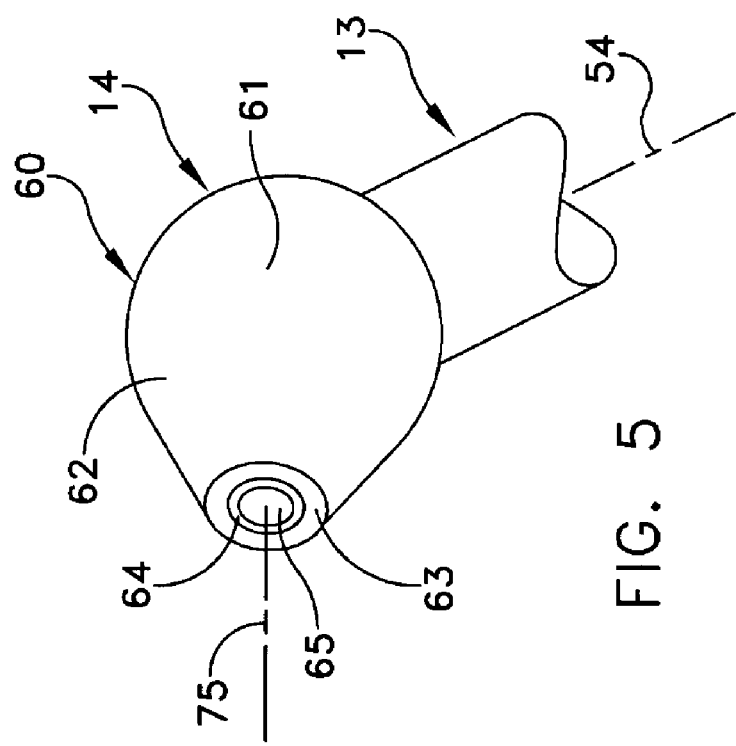
FIG. 5 is a perspective view of a probe tip taken from the distal end of the probe in FIG. 1.

Still referring to FIGS. 3 and 4, a tip 14 constructed in accordance with this invention attaches to the extension 13 in FIG. 3 and detaches from the extension 13 in FIG. 4. As it will become apparent, each tip 14 constructed in accordance with this invention has certain, common characteristics and features. Referring to FIGS. 3 through 5, each tip 14 is formed from a solid bulbous conductive material, such as brass, to form an outer conductor 60 with a main enlarged bulbous body portion 61 and a conical portion 62 that tapers to a measuring surface 63. The tip 14 carries an insulator 64 and a central conductor 65 in a first passage extending along a measurement axis 75 orthogonal to the measuring surface 63 described later. The surface 63 formed by the ends of the outer conductor conical portion 62, insulator 64 and center conductor 65 defines the measurement plane thereby to provide a sensing surface by which a measurement is obtained. As with the tube 41, the surface of the outer conductor 60 will be coated with an insulating material.

The center conductor 65 has an enlarged shank portion 66 and a narrower portion 67 delimited by a shoulder 70. The end of the narrower shank 67 terminates in a semispherical conductor portion 71. The insulator 64, that is positioned in the conical section 62, overlies the larger shank portion 66 and has a cylindrical body 72 with a collar 73 that engages the shoulder 70. The reduced shank portion 67 including the semispherical tip 71 is isolated from the outer conductor 60. It will also be apparent that the center conductor 67 extends to intersect the probe axis 54.

The outer conductor 60 also includes a planar surface 74 that lies in a plane that is normal to another axis that, in FIGS. 3 and 4, is coincident with the probe axis 54. This first axis and probe axis 54 are angularly offset from the measurement axis 75 normal to the planar surface 63 at an angle β. More specifically, an internally threaded hole or passage 76 extends in the direction along an axis 77, as the first axis, that is perpendicular to the planar surface 74 and coincident with the probe axis 54. The angle β between the measurement axis 75 and the axis 77 defines the angular aspect of the measurement plane for the given probe tip 14. In this specific embodiment β= 45°.

A complementary electromechanical connection provides a means for mounting a detached probe 14, as shown in FIG. 4. onto the distal end of the extension 13 as shown in FIG. 3. Specifically, it is merely necessary to screw the tip 14 onto the threaded head portion 44 as shown in FIG. 3 whereby the axis 77 and probe axis 54 are coincident. As rotation of the probe tip 14 relative to the extension 13 continues, the probe tip 14 advances proximally until the semispherical conductor portion 71 engages and makes electrical contact with the distal end of the center conductor 52 of the assembly 50. The structures will be dimensioned so that this contact occurs prior to engagement of a radial shoulder that defines the planar surface 74 and the shoulder 45. Further advancement and tightening of the probe tip 14 advances the probe tip 14 proximally and forces a displacement of the center conductor 52 against the bias of the internal spring of the assembly 50. A comparison of FIGS. 3 and 4 depicts this displacement. As a result the center conductor 52 and the center conductor 65 maintain good electrical contact. The outer conductor 60 has good electrical contact with the tube 40 by virtue of the threaded engagement.

Figure 7:
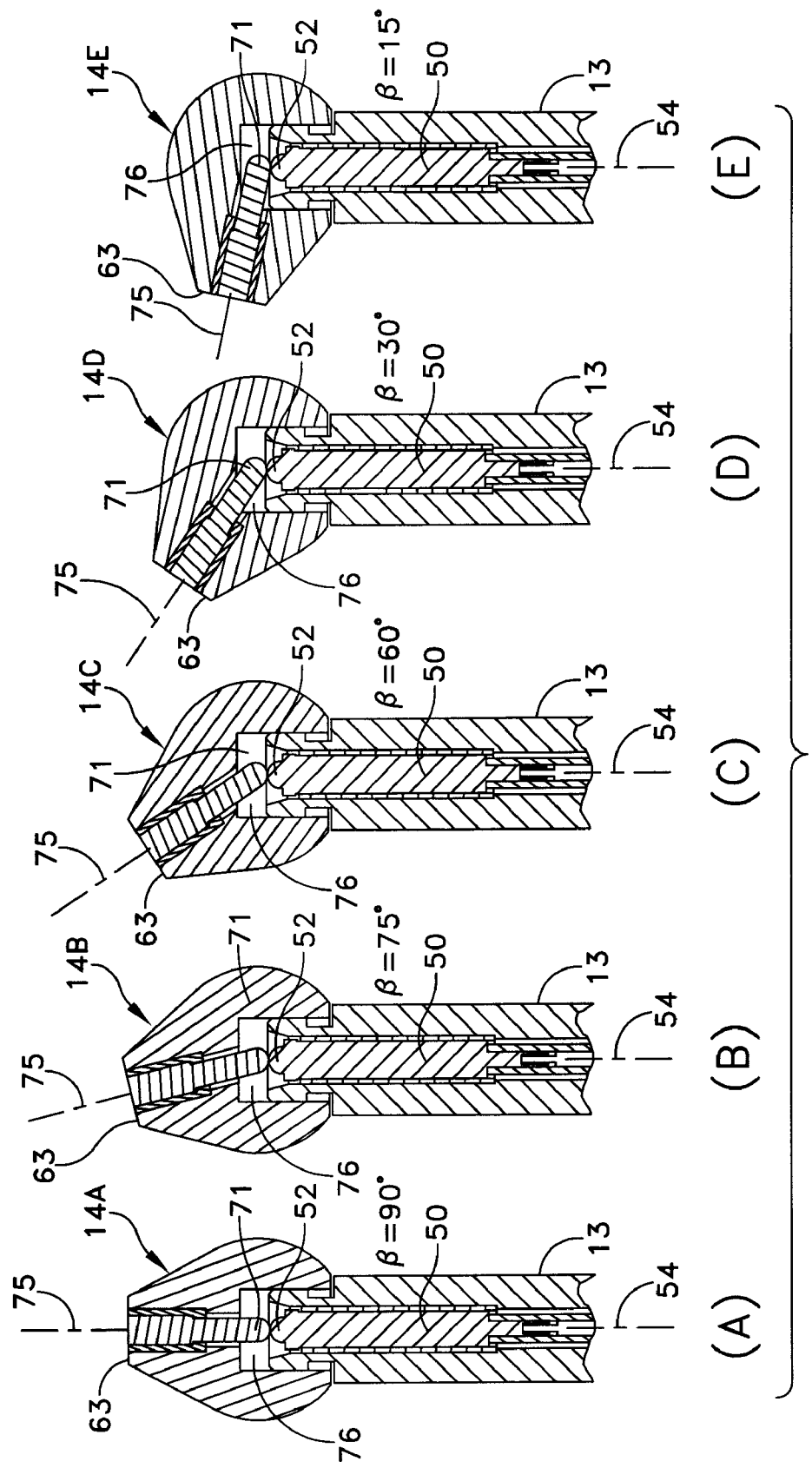
FIG. 7 depicts probe tips at (A) through (B) with different aspects between the measurement plane and probe axis.

To achieve the articulation function, a measurement system as shown in FIG. 1 can be constructed with a set of a plurality of probe tips 14 each of which provides a different angular aspect between the probe axis and the measurement plane. While FIGS. 2 through 6 depict a probe with an angular aspect of 45°, FIG. 7 depicts probes (A) through (E) with the measurement plane defined by the end 63 surface at different angular aspects. That is, each differs by the orientation of the probe axis 54 and coincident first axis (not shown in FIG. 7) and the measurement axis 75. For example, FIG. 7A depicts a probe tip 14 that provides a 90° aspect of the measurement plane defined by the surface 63 and the probe axis 54. In this particular case the hole 76 extends along the axis 75. Contact with the center conductor 52 is shown. At (B) in FIG. 7a tip 14B in which the axis 75 through the hole 76 is offset to provide a 75° aspect. The probes at (C) through (E) depict distal tips 14C, 14D and 14E, which provide aspects of 60°, 30° and 15° respectively.

Figure 8:
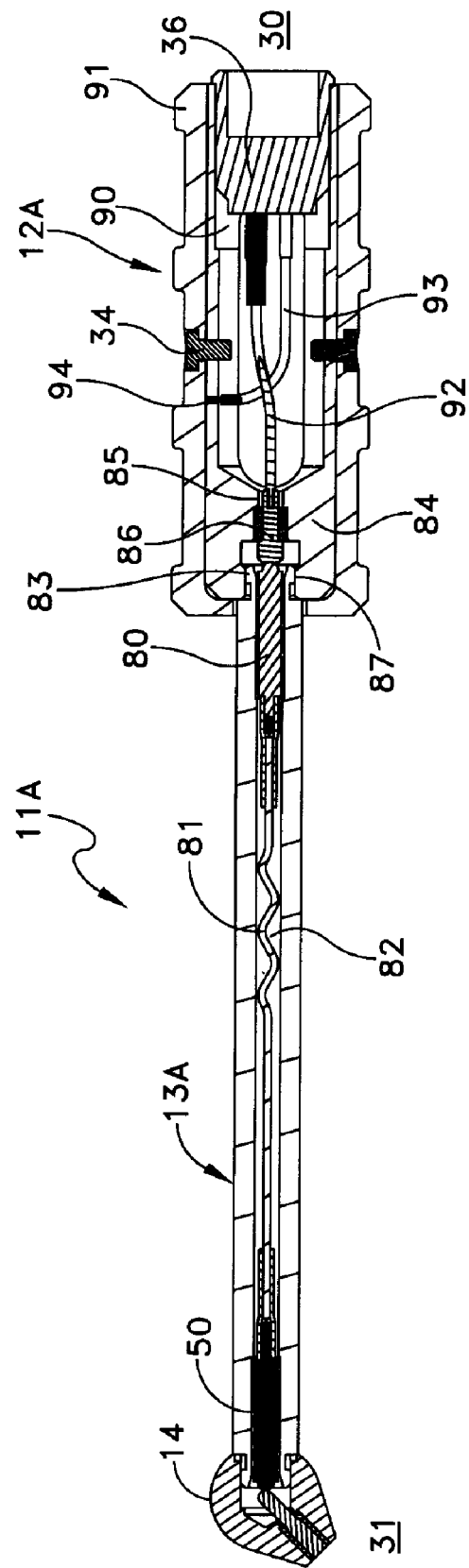
FIG. 8 depicts a longitudinal cross section of another embodiment of a probe.

The probe 111 shown in FIG. 2 provides replaceable probe tips 14 that can attach and detach from an extension 13 that is fixed in the handle 12. In some situations the examination process may contaminate the surface of the extension. Therefore it would be helpful if the extension were also replaceable. FIG. 8 depicts a modified probe 11A that achieves this objective. As many of the components in the probe 11A are similar to those in the probe 11 of FIGS. 2 through 4, like numerals are used to designate like elements. Modified elements are designated by different references numerals annotated with "A".

Referring to FIG. 8, the probe 11A has a replaceable tip 14 attached to the distal end 31 of the modified extension 13A. The modified extension 13A connects at its proximal end to a modified handle 12A. The interface between replaceable tips, such as the replaceable tip 14, with different aspects and the distal end of the extension in probe 11A is the same as shown with respect to the probe 111 in FIGS. 2 through 4. Consequently, no further discussion of this connection is necessary.

The modification to the extension 13A involves the termination at the proximal end. With this modification the proximal end of the extension 13A contains a spring biased conductor assembly 80, like the spring biased conductor assembly 50. A conductor 81 in a passage 82 connects the spring biased conductor assemblies 50 and 80. The modified extension 13A also terminates at a distal end with an externally threaded portion 83.

The handle 12A includes a central conductive body 84 with a central passage 85 that receives a fixed conductor 86. The distal end of the central conductive body 84 incorporates an internally threaded socket 87. With this configuration rotating the extension 13A relative to the handle 12A provides attachment or detachment of the extension 13A and the handle 12A. The interaction of the spring biased conductor assembly 80 and the conductor 86 provides the necessary signal path to the connector 36 located in a proximal receptacle 90. The modified extension 13A therefore is an independent structure or subassembly that can be handled separately from both the replaceable probe tip 14 and the handle 12A.

The handle 12A additionally includes an insulating cover 91 overlying the central conductive body 84. Machine screws 34 coated of a plastic material affix the insulating cover to the central conductive body 84. A conductor 92 provides a signal connection to the conductor 86. A ground connector 93 extends from the connector 36 to a ground connection 94 formed with the central conductive body 84. Thus the conductive path established between the body of the distal tip 14, the body of the modified extension 13A and the central conductive body 84 is coupled back through the connector 36 to complete the sensing circuit.

As will now be apparent, this construction does provide the advantage of allowing modified extensions 13A to be removed and replaced easily at a diagnostic facility. Consequently it is more readily adapted for use in a medical facility. It may also be possible to apply the concept by implementing modified extensions 13A and handles 12A where the extensions 13A have different lengths. However, such a modification will require calibration of the dermal phase meter of FIG. 1 because changes in the length of the modified extension 13A can alter the electrical characteristics of the probe 11A.

This invention has been disclosed in terms of certain embodiments. It will be apparent that many modifications can be made to the disclosed apparatus without departing from the invention. For example, different electro mechanical connections using alternate conductive members and mechanical connections, such as a signal connection could be substituted. Differently shaped tips, extensions and handles could be substituted. Therefore, it is the intent of the append claims to cover all such variations and modifications of the specifically disclosed embodiments as are covered by the claims.

What is claimed is:

1. In a dermal phase meter system including a data processing system and a probe lying along a probe axis for providing input to the data processing system, said probe comprising:
   A) a set of probe tips, each probe tip including:
      i) an outer electrode with first connection means for attaching said probe tip to said probe along a probe tip connection axis,
      ii) a center electrode lying along a measurement axis perpendicular to a measurement surface defined by the outer and center electrodes, and
      iii) an insulating medium spacing said outer and center electrodes whereby the angle between said probe tip connection axis and said measurement axis for a given probe tip establishes an angular aspect between the probe axis and the measurement surface and different probe tips in said set establish different angular relationships,
   B) probe tip support means for carrying a selected probe tip including a housing extending along the probe axis having:
      i) a first connection means at a proximal end thereof for connection to the data processing system,
      ii) a second connection means extending along the probe axis for engaging said probe outer electrode extending along the probe tip connection axis,
      iii) a third connection means in said housing proximate said second connection means and extending along the probe axis, said third connection means including an axially linearly displaceable, spring-biased, rigid conductor connected to said first connection means, each probe center electrode engaging and displacing said rigid conductor proximally as said probe tip is connected to said probe tip support means whereby said probe can operate with interchangeable probe tips that establish different angular aspects between said probe and measurement axes.

2. A probe as recited in claim 1 wherein each of said probe tips in the set provide a range of angular aspects from 15° to 90° in steps of 15°.

3. A probe as recited in claim 1 wherein said probe tip support means includes a proximal handle and an extension on the probe axis extending distally from said handle.

4. A probe as recited in claim 3 wherein said probe tip support means includes means for releasably affixing said extension to said handle.

5. A probe as recited in claim 3 wherein said probe tip support means and said extension have complementary electromechanical means for enabling the attachment and detachment of said extension to said handle.

6. A probe as recited in claim 5 wherein said displaceable conductor assembly includes a spring and a linearly displaceable rigid conductor.

7. A probe for a dermal phase meter comprising:
   A) a handle having an externally insulated conductive body and a proximal electrical connector supported thereby,
   B) an externally insulated conductive tubular extension with a central passage along a probe axis attached to a distal end of said body, said extension having a threaded connection thereof and assembly with an axially linearly displaceable, rigid spring-biased conductor in said passage for being displaced along the probe axis, and C) a replaceable probe tip having an externally insulated conductive body and first and second passages lying on first and second intersecting axes, an insulator in said first passage and a conductor supported by said insulator extending into said second passage with an internally threaded portion extending along the second axis for attachment to and detachment from said threaded connection on said extension, the attachment of a probe tip causing said rigid conductor in said spring biased conductor assembly to be displaced thereby to make a connection therewith.

8. A probe as recited in claim 7 wherein said first and second axes have a predefined aspect and wherein said probe has additional probe tips for attachment and detachment to said extension with different aspects between their respective first and second axes.

9. A probe as recited in claim 8 wherein said handle includes means for releasably affixing said extension thereto.

10. A probe as recited in claim 8 wherein said handle has a conductor and a first threaded connection at the distal end thereof and said extension has an axially displaceable spring-biased electrode assembly in said extension central passage at the proximal end thereof and said proximal end having a threaded connection that complements the threaded connection at the distal end of said handle whereby said extension can be attached and detached from said handle.

11. A probe as recited in claim 10 including a conductor extending between said axially displaceable, spring-biased conductor assemblies.

* * * * *